United States Patent [19]

Hickling et al.

[11] Patent Number: 5,616,845
[45] Date of Patent: Apr. 1, 1997

[54] ACOUSTIC SENSOR SYSTEM FOR INSECT DETECTION

[76] Inventors: Robert Hickling, 323 Country Club Rd., Oxford, Miss. 38655; Peng Lee, P.O. Box 6398, University, Miss. 38677; Wei Wei, P.O. Box 5502, University, Miss. 38677; Shi-Tse Chang, P.O. Box 6283, University, Miss. 38677

[21] Appl. No.: 210,376

[22] Filed: Mar. 18, 1994

[51] Int. Cl.$^6$ .................................................. G01N 29/04
[52] U.S. Cl. .................................................. 73/584; 73/587
[58] Field of Search .......................... 73/587, 591, 570, 73/584, 571, 572, 865.6; 367/139, 136

[56] References Cited

U.S. PATENT DOCUMENTS

| | | | |
|---|---|---|---|
| 4,671,114 | 6/1987 | Litzkow | 73/587 |
| 4,809,554 | 3/1989 | Shade | 73/587 |
| 4,895,025 | 1/1990 | Betts | 73/587 |
| 4,937,555 | 6/1990 | Litzkow | 340/540 |
| 4,941,356 | 7/1990 | Pallaske | 73/587 |
| 4,991,439 | 2/1991 | Betts | 73/587 |
| 5,005,416 | 4/1991 | Vick et al. | 73/587 |
| 5,285,688 | 2/1994 | Robbins et al. | 73/587 |

*Primary Examiner*—Hezron E. Williams
*Assistant Examiner*—Helen C. Kwok
*Attorney, Agent, or Firm*—Walker, McKenzie & Walker, P.C.

[57] ABSTRACT

An acoustic sensor system for detection of insects in agricultural commodities. The system includes isolation structure for isolating the agricultural commodities from external noise and vibration, an improved acoustic sensor for detecting sound from within the agricultural commodities and for generating a signal in response to sound so detected, and a user recognizable output such as earphones or a light emitting diode for producing user recognizable output in response to signals generated by the acoustic sensor.

10 Claims, 4 Drawing Sheets

ACOUSTIC SENSOR SYSTEM FOR INSECT DETECTION

BACKGROUND OF THE INVENTION

1. Field of the Invention

The present invention relates, in general, to an acoustic system for detecting insects in agricultural commodities. The terms "insect" and "insects" are used herein as including adult insects, insect larvae, etc. The terms "commodity" and "commodities" are used herein as including cotton bolls, fruit, nuts, grain, wood, etc.

2. Information Disclosure Statement

Acoustic detection of insects in agricultural commodities such as grain, fruit, nuts, and wood has been known for a number of years.

The destruction caused by insects in harvested commodities is significant. About 10% of grain in the United States of America (U.S.) is destroyed by insects annually. Overseas the percentage is much higher, especially in Africa and parts of Asia. Importation of fruit containing insect larvae can cause infestations that are destructive to domestic fruit crops. Major efforts are made by the United States Department of Agriculture (USDA) to control infestations of the Mediterranean fruit fly in California and Florida. Fruit imported into the U.S. from countries suspected of being infested with quarantine insects is inspected by cutting samples open and searching for larvae. This method is time consuming, subject to human error, and destructive of fruit. The export of fruit and grain is similarly affected by insect infestations. Overseas importers often require exacting standards to ensure that fruit contains no quarantine insect larvae and that grain infestations are within defined limits.

Another agricultural problem is the destruction of cotton crops caused by insects such as the boll weevil and the pink bollworm. Major efforts are made by cotton growers in California, with the aid of USDA Animal Plant and Health Inspection Service scientists, to control the pink bollworm. Cotton bolls are gathered from the fields to determine if there is a pink bollworm infestation. The bolls are cut open and inspected in the same way as fruit. Again, this is time consuming and inefficient.

A preliminary patentability search in Class 73, subclasses 587 and 661, produced the following patents which are believed to be relevant to the present invention:

Shade et al., U.S. Pat. No. 4,809,554, issued Mar. 7, 1989, discloses an insect detector that uses an ultrasonic detecting device sensitive to frequencies in the 40,000 hertz range. Ultrasonic means above the frequency range of human hearing (20 to 20,000 hertz).

Because sound waves are strongly attenuated in grain at high frequencies, it is unlikely that the ultrasonic detector can detect insects in grain at distances more than a few millimeters.

Pallaske, U.S. Pat. No. 4,941,356, issued Jul. 17, 1990, discloses a process for detecting the presence of adult insects or insect larvae in a solid substrate such as wood. The process includes the steps of recording the vibration or noise caused by insects in the substrate, converting the recorded vibration or noise to digital form, and then comparing the digital data to reference data obtained by applying noise or vibration behavioral reference pattern data to a microcomputer. Pallaske is concerned with the signal analysis used to detect insects in solids such as wood, and to distinguish the insect sounds from other sounds. The drawings consist of flow charts with little indication of the hardware used.

Betts, U.S. Pat. No. 4,991,439, issued Feb. 12, 1991, discloses an apparatus for detecting the presence of insects in particulate matter having a vibration receiving structure physically contacting in an off-center location, a piezoelectric transducer structure, such as a crystal, for directly detecting the vibration in the particulate matter.

The principle of the sounding rod is used to detect insects within a body of grain. Longitudinal waves travel up the rod exciting an electrical response in the piezoelectric structure. The rod is sensitive mainly at its end which appears to have a relatively small surface area to receive sound waves from insects.

Additionally, the following patents are known to the inventors and are believed to be relevant to the present invention:

Betts, U.S. Pat. No. 4,895,025, issued Jan. 23, 1990, discloses an apparatus for non-invasively detecting the presence of hidden insects actively destroying an article. The apparatus includes a piezoelectric transducer which generates electrical signals in response to mechanical forces applied thereto, a probe or diaphragm in direct contact with the piezoelectric transducer and with the article for detecting vibration forces in the article and transferring such forces to the piezoelectric transducer, an amplifier for amplifying the portion of the electrical signals produced by the piezoelectric transducer represented by insects which may inhabit the article, and means for analyzing the electrical signals representative of the vibrations to identify the species within the article.

Litzkow et al., U.S. Pat. No. 4,671,114, issued Jun. 9, 1987, discloses an apparatus for detecting insect larvae in agricultural commodities. The apparatus includes at least one sound-detecting diaphragm for holding an agricultural commodity, a sound waveguide connected at one end to the diaphragm for conveying sound waves from the diaphragm, a transducer connected to the other end of the waveguide for converting sound waves in the waveguide to electrical signals, an amplifier for amplifying the electrical signals; and signal observation means connected to the amplifier for allowing the output of the amplifier to be observed. The waveguide in this apparatus tends to have a detrimental effect because it acts as a resonator distorting the insect sounds.

Litzkow et al., U.S. Pat. No. 4,937,555, issued Jun. 26, 1990, discloses an apparatus for detecting insect infestation in agricultural commodities. The apparatus may include a container for containing the agricultural commodity or a probe for being inserted into the agricultural commodity, and a piezoelectric means located with the container or attached to the probe for being placed in direct communication with the agricultural commodity and for generating electricity in response to vibration only of a frequency above about 500 hertz. It should be noted that placing the hard, plane piezoelectric surface in direct contact with grain, fruit, cotton boll or other agricultural commodity does not provide as good an interfacial acoustic match as the diaphragm or liquid-filled cushion in our invention. Also the piezoelectric becomes less sensitive with pressure, such as would occur deep inside a grain silo.

None of the above identified patents or prior art discloses or suggests the present invention. More specifically, nothing in the known prior art discloses or suggests an apparatus for detecting insects in agricultural commodities including isolation means for isolating the agricultural commodities from external noise and vibration; sensitive acoustic sensor means for detecting any sound from the agricultural commodities and for generating a signal in response to any sound so detected; and user recognizable output means for producing user recognizable output in response to signals generated by the acoustic sensor means.

SUMMARY OF THE INVENTION

The present invention provides an apparatus for quickly, accurately and inexpensively inspecting agricultural commodities for insects. A basic concept of the present invention is to provide an insect detecting apparatus including isolation means for isolating the agricultural commodities from external noise and vibration; improved acoustic sensor means for detecting any sound from the agricultural commodities and for generating a signal in response to any sound so detected; and user recognizable output means for producing user recognizable output in response to signals generated by the acoustic sensor means.

The present invention was developed initially to speed up inspection for pink bollworm in cotton bolls. Variants of the present invention can also be used to improve the efficiency of fruit inspection. Also, the present invention can be used on a production line to inspect nuts, such as the pecan which suffers from infestation by the pecan weevil, and other agricultural commodities that can be easily separated into individual components that can be tested with single or multiple-sensor arrays.

Insect sounds of larvae inside cotton bolls or in fruit are of a very low level. Generally the sounds are of larvae eating or moving about within the boll or fruit. Sensitive acoustic sensors are needed to detect these sounds. Also, it is necessary to remove the effect of background noise. That is, the measurements should be made within a container that provides noise and vibration isolation. A third requirement is a simple, rapid read-out of results. Finally, the system has to be inexpensive and durable.

BRIEF DESCRIPTION OF THE DRAWINGS

FIG. 5B is a schematic diagram of another portion of an electrical circuit of the present invention and which, taken together with FIG. 5A, fully discloses the electrical circuit of the present invention.

DESCRIPTION OF THE PREFERRED EMBODIMENT

The preferred embodiment of the apparatus of the present invention is shown in FIGS. 1–7 and identified by the numeral 11. The apparatus 11 is especially designed to detect insects in agricultural commodities C.

The apparatus 11 includes one or more sensing units for detecting any sound from within the commodities C and for generating a signal in response to any sound so detected.

Figure 2:
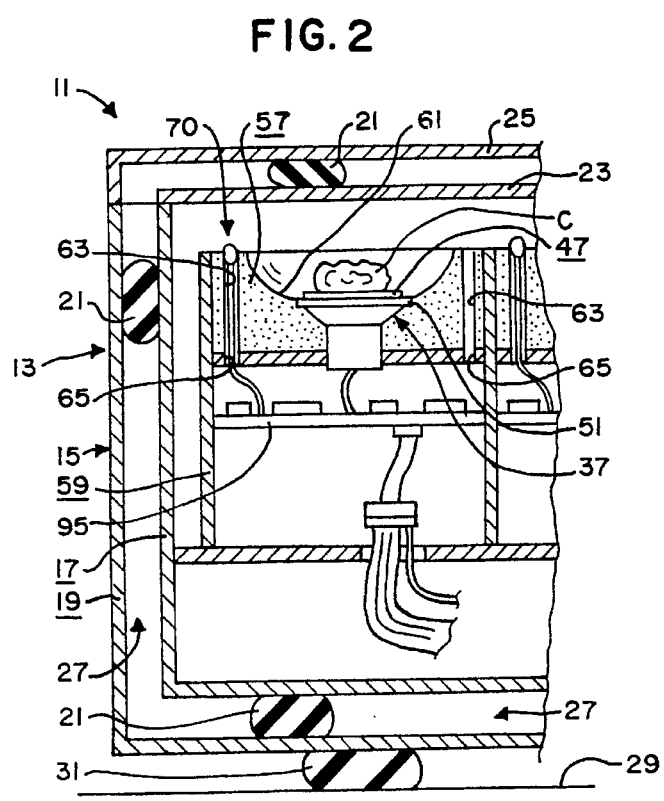
FIG. 2 is a sectional view of one of the sensor units on a somewhat enlarged scale compared to FIG. 1, showing the various parts of the sensor unit together with some of the details of the isolation means.

The apparatus 11 includes isolation means 13 for isolating the sensing units and the commodities C from external noise and vibration. The isolation means 13 preferably includes an isolation box 15 having a hollow interior for housing the commodities C and vibration isolating mounts for limiting the passage of external noise and vibration to the commodities C within the interior of the isolation box 15. The isolation box 15 preferably includes an inner box member 17 having a hollow interior for housing the sensing units and the commodities C and an outer box member 19 having a hollow interior for housing the inner box 17. The vibration isolation mounts preferably include interior vibration isolation mounts 21 positioned between the inner and outer boxes 17, 19 as shown in FIG. 2. The inner box 17 preferably has an openable top member or lid 23 for allowing access to the hollow interior thereof. Likewise, the outer box 19 preferably has an openable top member or lid 25 for allowing access to the hollow interior thereof.

Figure 1:
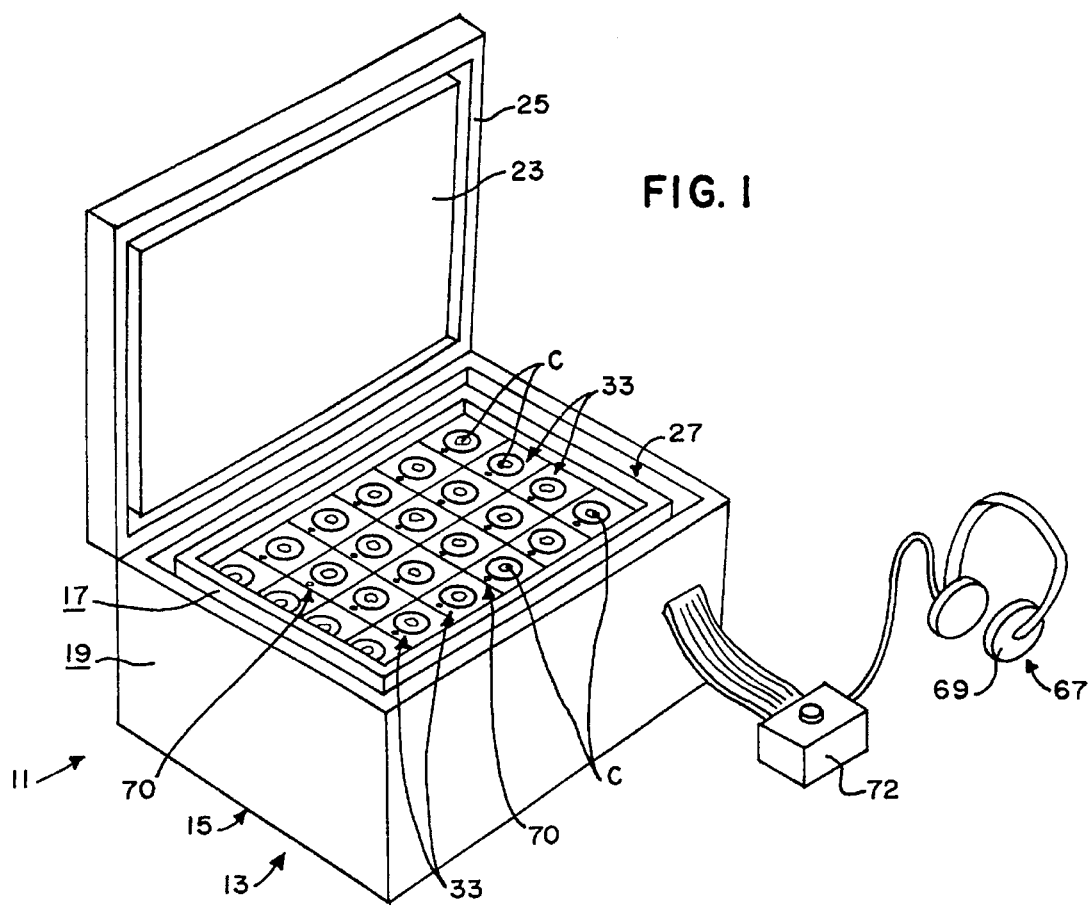
FIG. 1 is a perspective view of the preferred embodiment of the apparatus of the present invention for detecting insects in agricultural commodities, with the inner and outer boxes of the isolation means thereof opened, showing an array of sensor units in the inner box.

Each lid 23, 25 closes tightly to prevent airborne sound entering the interior of the associated box 17, 19. Each box 17, 19 is preferably made of rigid, heavy material, such as steel, that prevents the passage of sound through it. There is preferably an air gap 27 between the inner box 17 and the outer box 19 as shown in FIGS. 1 and 2 which aids in preventing the passage of sound from the outside into the interior of the inner box 17.

The vibration isolation mounts 21 support the inner box 17 inside the outer box 19 to limit the passage of structure borne sound. There is preferably no point of contact between the inner and outer boxes 17, 19 except through the isolation mounts 21. The vibration isolation mounts 21 may consist of rubber spacers or the like mounted in the air gap 27 between the inner and outer boxes 17, 19 as shown in FIG. 2.

It is important also to isolate the outer box 19 from outside vibrations, particularly from surfaces 29 such as a table or the like on which the outer box 19 may be resting. This can be accomplished by means of exterior isolation mounts 31 supporting the outer box 19 (see FIG. 2), or an isolation mat (not shown), etc. Contact with the other exterior sides of the outer box 19 should be avoided. If this is not possible, contact should be made through additional exterior isolation mounts or the like. The exterior isolation mounts 31 may consist of rubber spacers or the like mounted to the exterior surface of the outer box 19.

The sensing units of the apparatus 11 includes at least one acoustic sensor means 33 for detecting any sound from within the commodities C and for generating a signal in response to any sound so detected. The apparatus 11 preferably includes a plurality of sensor means 33 forming an array of sensor means 33 for simultaneously testing a plurality of individual pieces of agricultural commodity C (e.g., a plurality of individual cotton bolls, etc.), as clearly shown in FIG. 1.

Each sensor means 33 preferably includes an electrostatic microphone 35 located within the inner box 17 of the isolation box 15 for producing an electric signal that corresponds to sound from within the agricultural commodities C. The microphone 35 preferably consists of a typical electret microphone, well known to those skilled in the art. Sensitive electret microphones can be obtained cheaply. They are standard items in many audio electronic systems, but, for use in the present invention, should be selected for maximum sensitivity. Thus, PC-mount electret mike elements, model 270-090, as marketed by the Radio Shack division of Tandy Corp., Forth Worth, Tex. 76102, having a wide 20–15,000 hertz response could be used. Preferably, electret microphones having a −43 to −45 decibel sensitivity are used.

Each sensor means 33 preferably includes a stethoscope head 37 (see FIGS. 2, 3 and 4) surrounding the microphone 35 for increasing the sensitivity of the microphone 35 in the desired frequency range of around 1,000 hertz as will now be apparent to those skilled in the art. The stethoscope head 37 preferably includes an opened funnel or bell shaped body 39 formed from rigid plastic or the like to create a conical expansion chamber or cavity 41. The body 39 has a first or small end 43 connected to the microphone 35 and has an opened second or large end 45.

Figure 3:
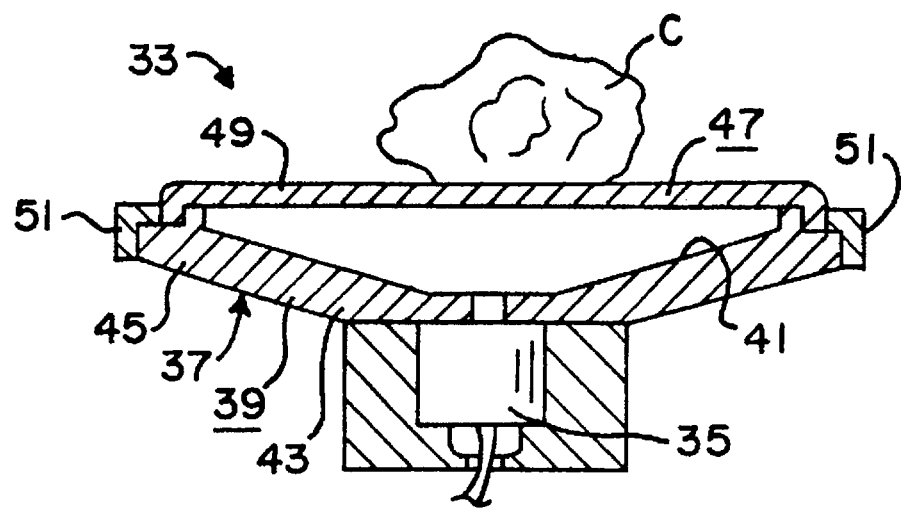
FIG. 3 is a sectional view of a portion of the apparatus of the present invention, showing a first embodiment of an acoustic sensor means thereof on a somewhat enlarged scale as compared to FIG. 2.
Figure 4:
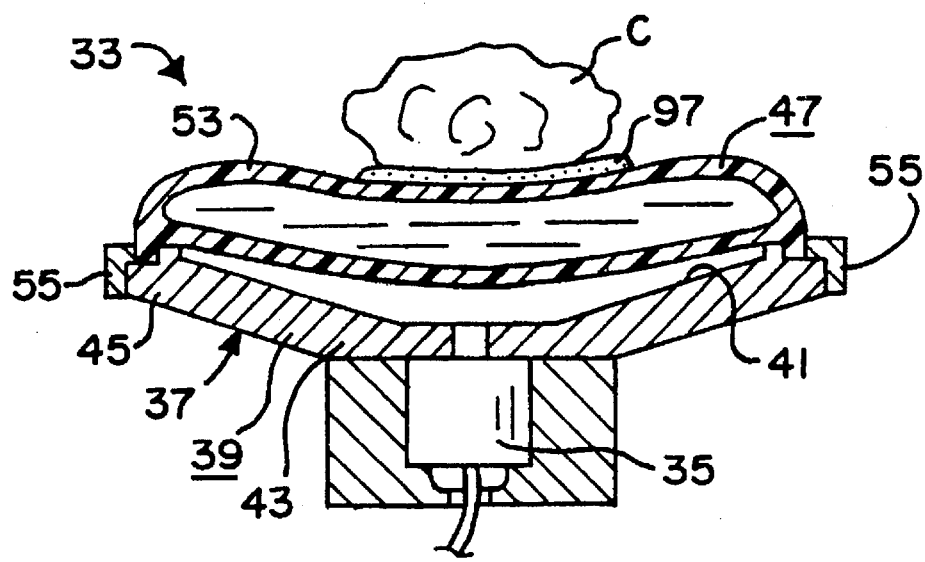
FIG. 4 is a sectional view similar to FIG. 3 but showing an alternate embodiment of the acoustic sensor means thereof.
Figure 5:
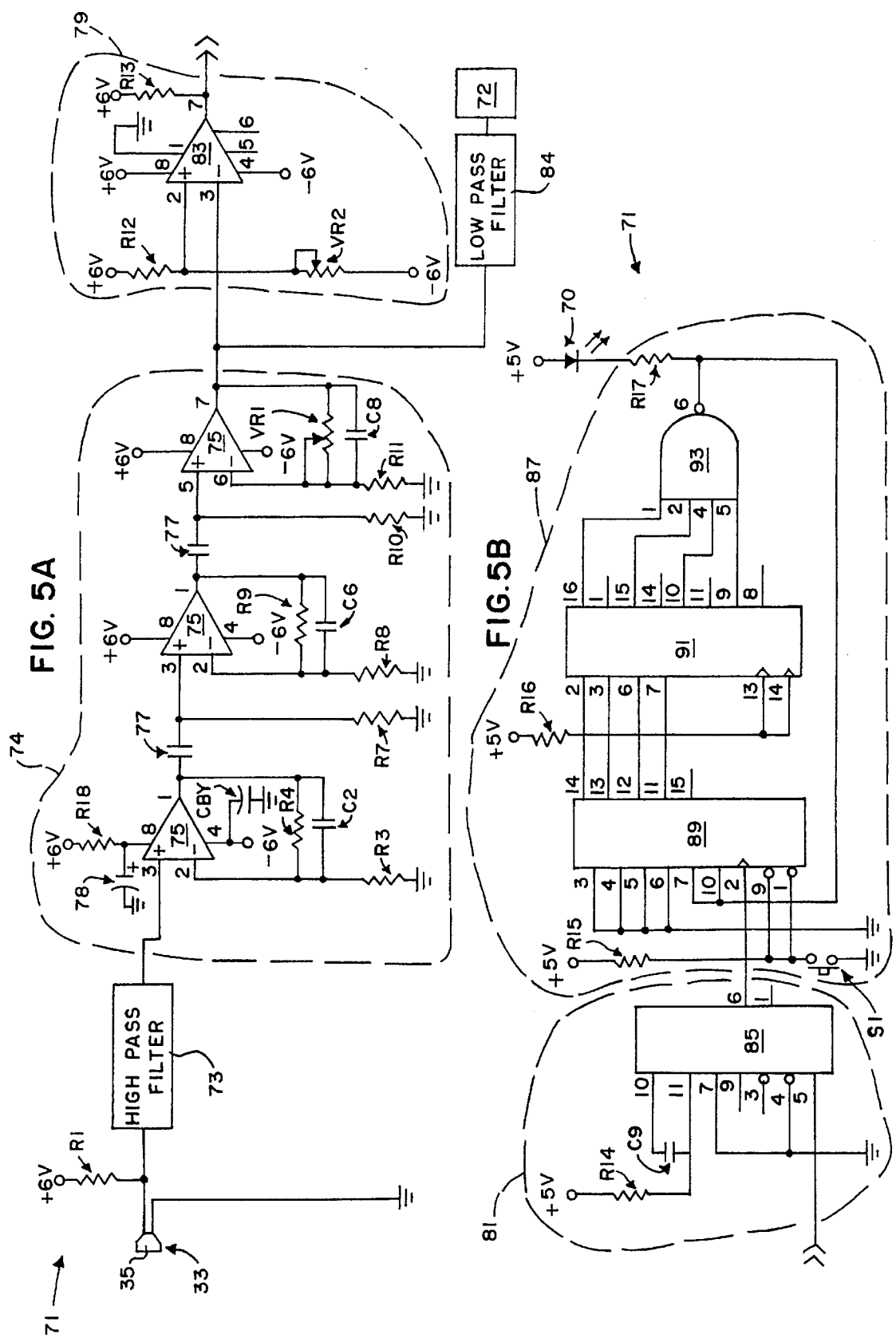
FIG. 5 A is a schematic diagram of a portion of an electrical circuit of the present invention.
Figure 6:
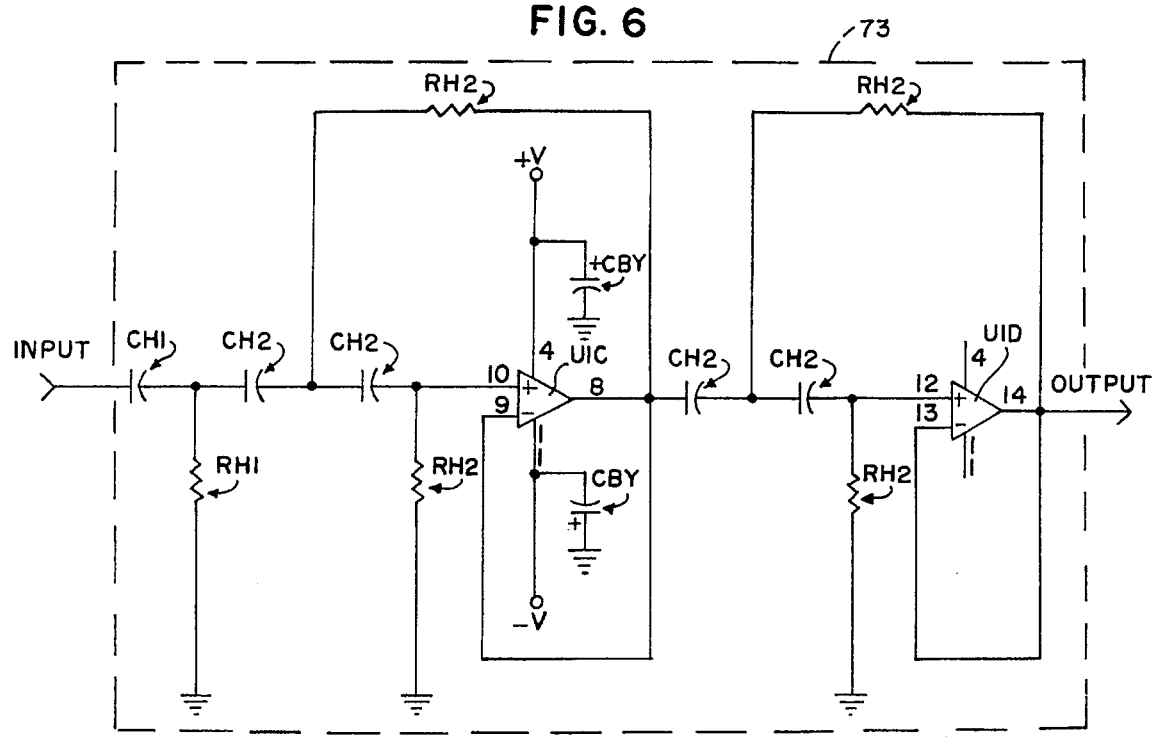
FIG. 6 is a schematic diagram of a preferred embodiment of a high pass filter of the electrical circuit of the present invention.
Figure 7:
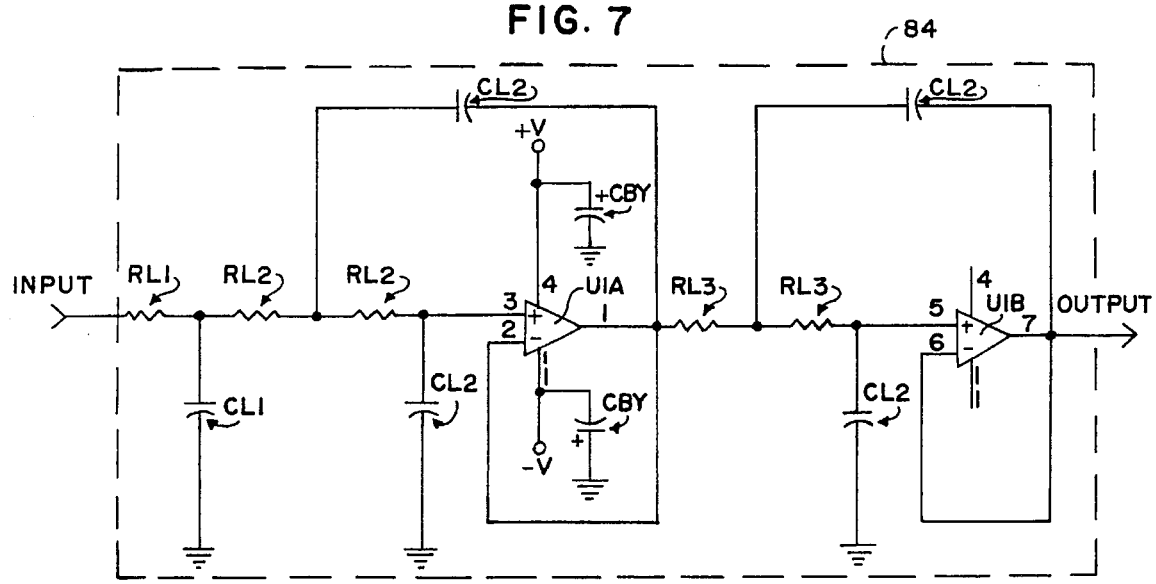
FIG. 7 is a schematic diagram of a preferred embodiment of a low pass filter of the electrical circuit of the present invention.

The second end 45 of the body 39 is preferably covered by a diaphragm 47, closing the conical cavity 41, as clearly shown in FIGS. 3 and 4. The increased sensitivity of the sensor means 33 around the desired frequency (i.e., around 1,000 hertz) is due, in large part, to the characteristics of the diaphragm 47, including the thickness and tension thereof. The frequency range of greatest sensitivity of the sensor means 33 can thus be adjusted by changing the characteristics of the diaphragm 47. Various types of diaphragm material have been tested. The commodities C to be tested are positioned directly on top of the diaphragm 47 as clearly shown in FIGS. 2, 3 and 4.

A first embodiment of the diaphragm 47 is shown in FIGS. 2 and 3 and includes a substantially plate-like membrane 49 attached to the body 39 over the opened second end 45 thereof by a ring 51 or the like. The membrane 49 may be constructed out of various materials in various thicknesses, etc., to provide different specific characteristics. A standard plastic membrane has been found to give optimum sensitivity around 900 hertz, while a membrane constructed out of metal shim stock has been found to give optimum sensitivity at higher frequencies of between 1,000 and 2,000 hertz. The frequency of optimum sensitivity can be adjusted by varying the thickness of the membrane 49 as well as the membrane material. Inserting the microphone in a stethoscope head 37 typically makes the sensor means 33 more sensitive in the frequency range around 1,000 hertz. Sensitivity in this frequency range is optimum, because it avoids the frequency range where vibration and background noise is generally strongest, i.e., low frequencies below about 500 hertz. Also high-frequency sound above about 1,500 hertz, due to larvae eating and moving, is attenuated by the material of the fruit or cotton boll. Hence, signals are usually clearest at intermediate frequencies around 1,000 hertz. The increased sensitivity of the sensor around 1,000 hertz is due, at least in part, to the characteristics of the membrane 49 caused by thickness and tension of the membrane 49, etc. The frequency range of greatest sensitivity of the sensor means 33 can thus be adjusted, as required, by changing the characteristics of the membrane 49.

A second embodiment of the diaphragm 47 is shown in FIG. 4 and includes a liquid-filled bag or cushion 53 attached to the body 39 over the opened second end 45 by a ring 55 or the like. The cushion 53 closes the second end 45 of the body 39 of the stethoscope head 37 and provides better acoustic transmission from the surface of the agricultural commodities C to the air in the body 39 of the stethoscope head 37. The liquid in the cushion 53 is preferably oil or some other suitable liquid. The cushion 53 adjusts itself to the surface of the agricultural commodities C so that vibrations are transmitted across a larger surface area providing a stronger signal at the microphone 35. Better transmission can also be achieved if the conical cavity 41 is filled with oil or other suitable liquid. This requires an adaptation of the microphone 35 to protect it from long-term exposure to the liquid.

Each sensor means 33 is preferably mounted in a cup 57 or the like which is, in turn, mounted to a base or frame 59 secured within the interior of the inner box 17 as shown in FIG. 2. The cup 57 preferably has a concaved depression 61 in the top surface thereof with the sensor means 33 mounted therein so that the diaphragm 47 is located at the bottom of the depression 61. The size of the depression 61 and the overall size of the diaphragm 47, etc., depends on the application. Thus, for example, for cotton bolls, most nuts and smaller fruit, the depression would typically have a diameter of about 3 to 4 inches (76.2 to 101.6 millimeters). For larger fruit and nuts, the size would be greater. For vibration isolation, the cup 57 is preferably made of molded plastic or other suitable material, and the base 59 is preferably made of plastic or other suitable material. Typically, the cup 57 and base 59 are attached to the outer surface of the body 39 of the stethoscope head 37 and to each other with an adhesive bonding. Air passageways 63 are preferably provided through the cup 57 and mating air passageways 65 are preferably provided through the base 59 to allow heat to rise therethrough for reasons which will hereinafter become apparent.

The apparatus 11 includes user recognizable output means for producing a user recognizable output in response to signals generated by the sensor means 33. The user recognizable output means preferably includes an audio output means 67 for producing an audio output in response to any signal generated by the sensor means 33. The audio output means 67 preferably includes earphones 69 or the like (see FIG. 1). The user recognizable output means preferably includes visual output means, such as a typical light emitting diode (LED) 70 or the like (see FIG. 5B) for producing a visual output in response to signals generated by the sensor means 33. The LED 70 is preferably located so that it is visible when the diaphragm 47 is viewed. Thus, as clearly shown in FIGS. 1 and 2, the LED 70 is preferably located on the upper surface of the cup 57.

As above indicated, the apparatus 11 preferably includes a plurality of sensor means 33 arranged in an array within the inner box 17. The array may consist of 48 evenly spaced sensor means 33. Each sensor means 33 may have its own electric circuit 71. Any number of sensor means 33 can be used depending on the application.

The specific electric circuit 71 used to couple the microphone 35 of the sensor means 33 to the earphones 69 and or LED 70 may vary depending on the sensitivity desired, etc. The preferred embodiment of one specific electric circuit 71 used to couple the microphone 35 of one specific sensor means 33 to an earphone selector switch 72 and to an LED 70 is shown schematically in FIGS. 5A and 5B. The earphone selector switch 72 may consist of any typical a multi-position switch for allowing the user of the earphones 69 to switch from one sensor means 33 to another using standard electrical switching devices, such as a rotary switch or combination of rotary switches for the columns and rows in the array of sensors, as will now be apparent to those skilled in the art.

The sensor means 33 shown in FIG. 5A will generally be the microphone 35 of the sensor means 33 shown in FIGS. 3 and 4, which is used to detect larvae in cotton bolls, and in certain kinds of fruit. The electric circuit 71 may includes a resistor R1 as shown in FIG. 5A and which, for an given dynamic range, may consist of standard 10 kilohm resistor which provides microphone 35 with a bias current. Signals from the sensor means 33 are preferably passed through a high-pass filter 73 that allows frequencies above about 800 hertz to pass therethrough, and then through an amplifier circuit 74. The high-pass filter 73 may consist of a typical high-pass active filter of any specific construction now apparent to those skilled in the art. One embodiment of such a typical high-pass filter 73 may include a pair of operational amplifiers U1C and U1D, preferably low noise LM837 operational amplifiers, manufactured by Texas Instruments, P.O. Box 655474, Dallas, Tex. 75265 or the equivalent, resistors RH1 and RH2, and capacitors CH1, CH2 and CBY electrically coupled as clearly shown in FIG. 6. For a given operating frequency range, the resistors RH1 and RH2 may consist of standard 10 kilohm resistors, the capacitors CH1 and CH2 may consist of standard 0.068 microfarad capacitors, and the capacitor CBY may consist of a standard 220 microfarad capacitor. The amplifier circuit 74 may include a plurality of operational amplifiers 75, preferably low noise LM837 operational amplifiers, manufactured by Texas Instruments, P.O. Box 655474, Dallas, Tex. 75265 or the equivalent, joined by typical coupling capacitors 77, as will now be apparent to those skilled in the art. A polarized capacitor 78 is preferably provided as shown in FIG. 5A for preventing instability when a plurality of circuits 71 are hooked together and connected to a single motherboard for providing power, etc. The amplifier circuit 74 may also include resistors R3, R4, R7, R8, R9, R10, R11 and VR1, and capacitors C2, C6, C8 and CBY electrically coupled as clearly shown in FIG. 5A. For an given amplification range, resistors R3, R8 and R11 may consist of standard 1 kilohm resistors, the resistors R4 and R9 may consist of standard 50 kilohm resistors, the resistors R7 and R10 may consist of standard 18 kilohm resistors, the resistor VR1 may consist of a standard 50 kilohm variable resistor, the capacitors C2 and C8 may consist of standard 30 picofarad capacitors, the capacitor C6 may consist of a standard 0.001 microfarad capacitor, the capacitors 78 and CBY may consist of standard 220 microfarad capacitors, and the capacitors 77 may consist of standard 0.1 microfarad capacitors.

The signals from the amplifier circuit 74 may then pass through a comparator circuit 79 and then a timer circuit 81. The comparator circuit 79 determines signals that are above a certain trigger level. Its output consists of a signal that is low when the input 2O signal is below the trigger level and a high when the input signal is above the trigger level. The comparator circuit 79 includes a voltage comparator 83, preferably an LM311 voltage comparator, manufactured by National Semiconductor, 2900 Semiconductor Drive, Santa Clara, Calif. 95051, or the equivalent, as shown in FIG. 5A and as will now be apparent to those skilled in the art. The comparator circuit 79 may also include resistors R12, R13 and VR2 electrically coupled as clearly shown in FIG. 5A. Resistor R12 may consist of a standard 10 kilohm resistor, resistor R13 may consist of a standard 2 kilohm resistor, and resistor VR2 may consist of a standard 20 kilohm variable resistor.

Signals from the amplifier circuit 74 may also pass through a low pass filter 84 that allows frequencies below about 3,000 hertz to pass to the earphone selector switch 72 as shown in FIG. 5A. The low pass filter 84 may consist of a typical low-pass active filter of any specific construction now apparent to those skilled in the art. One embodiment of such a typical low-pass filter 84 may include a pair of operational amplifiers U1A and U1B, preferably low noise LM837 operational amplifiers, manufactured by Texas Instruments, P.O. Box 655474, Dallas, Tex. 75265 or the equivalent, resistors RL1, RL2, and RL3, and capacitors CL1, CL2 and CBY electrically coupled as clearly shown in FIG. 7. For a given operating frequency range, the resistors RL1, RL2 and RL3 may consist of standard 10 kilohm resistors, the capacitor CL1 may consists of a standard 0.0033 microfarad capacitor, the capacitor CL2 may consist of a standard 0.0015 microfarad capacitors, and the capacitor CBY may consist of a standard 220 microfarad capacitor. The high pass filter 74 and the low pass filter 84 coact with one another to create, in effect, a band-pass filter that excludes background noise and vibration below about 800 hertz and high-frequency noise above about 3,000 hertz, concentrating the signals in the frequency range between 800 hertz and 3000 hertz.

The timer circuit 81 controls the duration of the high signal from the comparator to a typical time period between bites of an insect (e.g., a larva) inside a piece of agricultural commodity C, such as a cotton boll, a piece of fruit, or a nut. This time period is determined experimentally, beforehand, depending on the type of insect being tested for, etc. Typically, it is about 20 milliseconds. The timer circuit 81 preferably includes a monostable multivibrator 85, preferably a 74121 monostable multivibrator, manufactured by National Semiconductor, or the equivalent, as shown in FIG. 5B and as will now be apparent to those skilled in the art. The timer circuit 81 may also include resistor R14 and capacitor C9 electrically coupled as clearly shown in FIG. 5B. Resistor R14 may consist of a standard 100 kilohm resistor, and capacitor C9 may consist of a standard 0.33 microfarad capacitor.

After this period, the output of the timer circuit 81 is switched to a constant low, where it remains until the next high signal comes from the comparator circuit 79. Thus, a series of high signals of a fixed maximum duration determined by the timer circuit 81, with intervals of low signals in between, is fed to a counter circuit 87 which counts the number of high signals. If this number exceeds certain value, for example, fifteen within a ten second period, the LED 70 is energized (i.e., lit), indicating the presence of an insect within the agricultural commodity C being tested. The counter circuit 87 preferably includes a presettable binary counter 89, preferably a 74LS 161 presettable binary counter, manufactured by National Semiconductor, or the equivalent; a quad latch 91, preferably a 74LS75 quad latch, manufactured by National Semiconductor, or the equivalent; and a dual 4-input NAND gate 93, preferably a 74LS20 dual 4-input NAND gate, manufactured by National Semiconductor, or the equivalent, as shown in FIG. 5B and as will now be apparent to those skilled in the art. The counter circuit 87 may also include resistors R15, R16 and R17, and reset switch S1 electrically coupled as clearly shown in FIG. 5B. For a given operating range of the counter, resistors R15 and R16 may consist of standard 10 kilohm resistors and resistor R17 may consist of a standard 220 ohm resistor.

The individual sensor means 33 performs this procedure simultaneously for an individual piece of agricultural commodity C, such as an individual cotton boll or piece of fruit on each sensor. The array of sensor means 33, such as that shown in FIG. 1, then indicates which piece of agricultural commodity C contains an insect and which does not, according to whether the LED 70 is lit or not. The individual components of the electric circuit are preferably electronic chips on a printed circuit board 95 (see FIG. 2). The components are readily obtainable and inexpensive. The board is small enough to fit below each sensor means 33. Electrical wires from the microphone 35 extend to the circuit board 95. The circuit board 95 is mounted to the base 59, typically with screws. Electrical wires extend from the circuit board 95 to the earphone selector switch 72 and to a power supply. The array of sensor means 33 may be operated with a common power supply through a common master switch (not shown).

To use the apparatus 11 shown in FIG. 1 to determine the presence of insects in a plurality of separate pieces of commodities C, the lids 23, 25 are opened and the separate pieces of commodities C are placed on separate diaphragms 47 so that each piece of commodity C is on an individual diaphragm 47 as clearly indicated in FIG. 1. The lids 23, 25 are then closed to isolate the commodities C from external noise and vibration. The array of sensor means 33 is then activated shortly after the lids 23, 25 of the isolation boxes 17, 19 are closed by closing the master switch of the common power supply, etc., and is deactivated after a given time interval, for example, ten seconds. After this time period has elapsed, all the circuits are frozen by shutting off the power supply to circuits 74 and 79, and the lids 23, 25 are opened and the LEDs 67 are examined to determine the number of pieces of agricultural commodity C containing insects.

Another way of determining the presence of insects in the commodities C is to use the earphones 69 connected to the sensor means 33 between the amplifier circuit 74 and the comparator circuit 79. Human ears are often more effective for determining weak larvae signals in a noise background especially in the early stage of larvae development. The acoustical signal strength of the larvae in cotton bolls or fruit can be increased by first immersing the bolls or fruit in warm water. The temperature of the water is such that it stimulates larva activity without harming the boll or fruit, or the larvae. To use this method, the lids 23, 25 are opened and the separate pieces of commodities C are placed on separate diaphragms 47 so that each piece of commodity C is on a individual diaphragm 47 again as clearly indicated in FIG. 1. The lids 23, 25 are then closed to isolate the commodities C from external noise and vibration. The array of sensor means 33 is then activated shortly after the lids 23, 25 of the isolation boxes 17, 19 are closed by closing the master switch of the common power supply, etc. However, rather than deactivating the sensor means 33 and opening the lids 23, 25, the earphones 69 are merely connected to the array and an operator merely listens to the output of each sensor means 33 one at a time using the rotary switch or the like so that the operator can decide whether each separate piece of commodity C is infested, etc., as will now be apparent to those skilled in the art.

As a result of vibration of the isolation box 15, the commodities C can move and rub on the surface of the diaphragm 47 of the sensor means 33, thereby generating an interference noise. To prevent this, a thin layer of adhesive 97 or other bonding substance can be used, between each piece of commodity C and the diaphragm 47 for adhering the commodities C to the diaphragm 47. The adhesive 97 should consist of a substance such as silicon jell or petroleum jelly or a putty that is not overly sticky, etc., and should be thin enough in the region of contact so that it does not attenuate transmission of acoustic signals from the commodities C. The concaved depression 61 in the cup 57 shown in FIG. 2 also serves to reduce the motion of the commodities C against the diaphragm 47.

Because the electronics are in a closed box with little circulation of air, it is necessary to ensure there is adequate cooling. This can be accomplished each time the box is opened by small cooling fans (not shown) that circulate the air via plastic tubes and the air passageways 63, 65 throughout the apparatus 11. Tests indicate that such cooling is probably not necessary for a 48-sensor, pink bollworm system.

A central digital controller or processor could be used in this invention to control the data-taking and functioning of the array of sensor means 33. Such a processor could function to interrogate each sensor means 33 and display the sensor data on a monitor screen, showing which sensor means 33 have detected larvae and which have not. This would probably be most useful in a production line system, for inspecting individual pieces of fruit, nuts or other commodity. This information would then be transmitted to automated devices that would remove the infested commodities from the production line and allow the uninfested commodities to proceed to subsequent stages of processing. The digital controller could also keep statistical records on the degree of infestation and how this varies with time. Also, it can monitor the performance of the sensor means 33 and the entire system. This could replace the LED display associated with each sensor means 33 described above. The LED displays and earphones would be more appropriate for use in the field, where there is not a production line system in operation. In addition, such a processor could function to provide digital processing to replace the circuits described above for each sensor means. It should be realized that each circuit represents a parallel processor which takes roughly 10 or more seconds to perform its function. The system of circuits described above represents an inexpensive way of performing the parallel processing. To do the data-taking digitally in sequence, one sensor means 33 at a time, would take too much time, i.e., on the order of minutes rather than seconds. To do the data-taking digitally in parallel would be costly. However, there may be situations where this would be desirable, e.g., for greater long-term reliability in a production line system.

The sensor means 33 and the specific circuits are designed to reduce the effect of background noise. However, to insure maximum accuracy, it is still necessary to enclose the sensor means 33 in the isolation box 15 to exclude background noise and vibration as much as possible. As above described, the isolation box 15 consists of a box within a box.

Although the present invention has been described and illustrated with respect to a preferred embodiment and a preferred use therefor, it is not to be so limited since modifications and changes can be made therein which are within the full intended scope of the invention.

We claim:

1. An apparatus for detecting insects in a plurality of separate units of agricultural commodities, said apparatus comprising:

(a) isolation means for isolating the plurality of separate units of agricultural commodities from external noise and vibration; said isolation means including an inner box member having an interior for completely enclosing the plurality of separate units of agricultural commodities, an outer box member having an interior for completely enclosing said inner box member, and vibration isolation mounts positioned between said inner and outer box members for limiting passage of external noise and vibration to the plurality of separate units of agricultural commodities completely enclosed within said interior of said inner box member;

(b) a plurality of acoustic sensor means housed within said interior of said inner box member; each of said plurality of acoustic sensor means including a diaphragm having a top surface for allowing one of the plurality of separate units of agricultural commodities to be positioned directly thereon, for detecting any sound from within the agricultural commodities and for generating a signal in response to any sound so detected; said acoustic sensor means including microphone means for generating a signal in response to any sound emitted from the separate units of agricultural commodities positioned directly on said top surface of said diaphragm thereof, and a stethoscope head surrounding said microphone means thereof;

(c) amplification means for producing an amplified signal in response to said signal generated by said plurality of acoustic sensor means; and (d) output means for producing a discernable output signal in response to said signal generated by said acoustic sensor means.

2. The apparatus of claim 1 in which said output means includes audio output means for producing an audio output in response to said signal generated by said acoustic sensor means.

3. The apparatus of claim 2 in which said audio output means includes earphones.

4. The apparatus of claim 1 in which said output means includes visual output means for producing a visual output in response to said signal generated by said acoustic sensor means.

5. The apparatus of claim 4 in which said visual output means includes a light emitting member for emitting light in response to said signal generated by said acoustic sensor means.

6. The apparatus of claim 1 in which is included adhesive for adhering the agricultural commodities to said diaphragm.

7. An apparatus for detecting an insect in a unit of agricultural commodity, said apparatus comprising:

(a) acoustic sensor means for detecting any sound from said unit of agricultural commodity and for generating a signal in response to any sound so detected;

(b) output means for producing a discernable output signal in response to said signal generated by said acoustic sensor means; and (c) isolation means for isolating the unit of agricultural commodity from external noise and vibration; said isolation means including an inner box member completely enclosing the unit of agricultural commodity and for housing said acoustic sensor means, and including an outer box member completely enclosing said inner box member; said isolation means including vibration isolation mounts positioned between said inner box member and said outer box member for limiting passage of external noise and vibration to the unit of agricultural commodity and said acoustic sensor means.

8. The apparatus of claim 7 in which said inner box member of said isolation means has an interior and an openable top member for allowing access to said interior thereof; and in which said outer box member of said isolation means has an interior and an openable top member for allowing access to said interior thereof.

9. The apparatus of claim 7 in which said acoustic sensor means includes an electret microphone and a stethoscope head surrounding said electret microphone.

10. The apparatus of claim 7 in which is included amplification means for producing an amplified signal in response to said signal generated by said acoustic sensor means.

* * * * *